United States Patent
Tan

(10) Patent No.: US 8,372,817 B2
(45) Date of Patent: Feb. 12, 2013

(54) SMALL INTERFERING RNA FOR GENE KNOCKDOWN OF THE SUBCUTANEOUS N-METHYL-D-ASPARTATE RECEPTOR NR1 SUBUNIT, AND IT'S APPLICATION ON PHARMACEUTICS

(75) Inventor: Ping-Heng Tan, Kaohsiung (TW)

(73) Assignee: I-Shou University, Kaohsiung County (TW)

( * ) Notice: Subject to any disclaimer, the term of this patent is extended or adjusted under 35 U.S.C. 154(b) by 136 days.

(21) Appl. No.: 12/780,278

(22) Filed: May 14, 2010

(65) Prior Publication Data

US 2011/0263676 A1 Oct. 27, 2011

(30) Foreign Application Priority Data

Mar. 11, 2010 (TW) .................................. 99107164 A

(51) Int. Cl.
  *A01N 43/04* (2006.01)
  *C12Q 1/68* (2006.01)
  *C12P 19/34* (2006.01)
  *C12N 15/63* (2006.01)
  *C07H 21/04* (2006.01)

(52) U.S. Cl. .......... 514/44; 435/6; 435/91.1; 435/91.31; 435/455; 536/23.1; 536/24.5

(58) Field of Classification Search .............. 435/6, 91.1, 435/91.31, 458, 455; 514/44; 536/23.1, 536/24.5
See application file for complete search history.

(56) References Cited

U.S. PATENT DOCUMENTS

| | | | |
|---|---|---|---|
| 5,502,166 A | * | 3/1996 | Mishina ........................ 530/350 |
| 6,924,109 B2 | | 8/2005 | Melcher et al. |
| 7,169,751 B2 | * | 1/2007 | Silos-Santiago et al. .... 514/18.3 |
| 7,399,586 B2 | | 7/2008 | Klinghoffer et al. |
| 7,687,080 B2 | | 3/2010 | Wolicki |
| 7,700,122 B1 | | 4/2010 | Kolesnikov et al. |
| 2007/0015145 A1 | * | 1/2007 | Woolf et al. ....................... 435/6 |
| 2008/0194089 A1 | * | 8/2008 | Pekarik et al. ................. 438/585 |
| 2008/0294089 A1 | * | 11/2008 | Hardy ............................. 604/22 |

FOREIGN PATENT DOCUMENTS

JP 2010/022227 * 2/2010

\* cited by examiner

*Primary Examiner* — Jane Zara

(74) *Attorney, Agent, or Firm* — Muncy, Geissler, Olds & Lowe, PLLC

(57) ABSTRACT

A small interfering RNA for gene knockdown of the N-methyl-D-aspartate receptor NR1 subunit comprises 21 to 25 ribonucleic acids, which are homologous to the RNA sequence of N-methyl-D-aspartate receptor NR1 subunit. A method of using the small interfering RNA, applying the small interfering RNA on subcutaneous tissues temporary interfere with the genetic expression of the NMDA receptor NR1 subunit in hypoderm. A use of the small interfering RNA on pharmaceutics, applying the small interfering RNA manufacture into new analgesic drugs for moderating the inflammatory pain or intolerable chronic pain, especially on clinical chronic pain and burn pain patients. An analgesic drug for skin inflammatory pain comprising: the small interfering RNA and a siRNA acceptable vehicle.

16 Claims, 16 Drawing Sheets

SMALL INTERFERING RNA FOR GENE KNOCKDOWN OF THE SUBCUTANEOUS N-METHYL-D-ASPARTATE RECEPTOR NR1 SUBUNIT, AND IT'S APPLICATION ON PHARMACEUTICS

BACKGROUND OF THE INVENTION

1. Field of the Invention

The present invention relates to a small interfering RNA, a method of using the small interfering RNA and a use of the small interfering RNA on pharmaceutics particularly to a N-methyl-D-aspartate receptor NR1 subunit small interfering RNA, a method of using the N-methyl-D-aspartate receptor NR1 subunit small interfering RNA to inhibit the expression of pain related gene in subcutaneous tissue, also a use of the N-methyl-D-aspartate receptor NR1 subunit small interfering RNA on pharmaceutics.

2. Description of the Related Art

Pain is an unpleasant sensory and emotional experience common to tissue damages, also a directly physiological response to any disease, trauma and infection. Pain is initiated by the stimulation (some damage of the peripheral or central nervous system) of nociceptors in the peripheral nervous system. Based on the persisting time, location, degree and type of pain, it is sufficient for determining the cause of pain. Generally, pain will only last until the stimulation is removed or the damage is healed, the incisional wound pain for example. However, some kind of pain, such as cancer and non-cancer chronic pain may persist for ages. For therapeutic concern, a pathologic pain or a pain lasting longer than 6 months (defined as chronic pain) needs proper treatments for relieving pain.

Nociception is defined as an unconscious feeling resulted from a noxious stimulation on the nociceptors in the peripheral or central nervous system. The noxious stimulation is initiated by chemicals, thermal, force or any trauma. Through the transmission of nociceptor, a stimulated signal is conveyed to the sensory neuron of spinal cord, inducing the secretion of glutamate (Glu). Generally, some tissue damages, inflammation or injuries will evoke a continuous release of Glu, leading to long-lasting membrane depolarization to prolong the noxious stimulation. In vertebrates, the Glu is a major excitatory transmitter of central nervous system, which can activate glutamate receptors (GluRs) in brain or spine, trigger neurotransmission, and finally result in pain. It is believed that the mechanism of Glu-related neurotransmission plays an important role both in normal nociception and pathophysiological nociception.

The Glu is released from the central terminals of spinal cord upon noxious stimulation, activating post-synaptically localized GluRs to cause pain. The GluRs are divided into two types, metabotropic GluRs and ionotropic GluRs, action of them are involved in different pain responses. In addition, ionotropic GluRs mainly mediate excitatory synaptic transmission in the spinal cord, comprising kainite, N-methyl-D-aspartic acid (NMDA) receptors and α-amino-3-hydroxy-5-methyl-4-isoxazole propionic acid (AMPA) receptors. Based on previous reports, NMDA receptors are widely localized on terminals in the spinal cord dorsal horn, which are presumed to provoke primary afferent, therefore, play a crucial role in excitatory synaptic transmission, plasticity and neurodegeneration.

NMDA receptors are composed of NR1, NR2 (including 4 subunits of A, B, C, and D) and NR3 (including subunit A and B) subunits. It is demonstrated that the functional formation of NMDA receptors channels essentially requires the combination of NR1 as a channel-forming subunit. The NMDA receptors control a cation channel that is highly permeable to calcium ($Ca^{2+}$) to activate the following mechanism of neurotransmission of pain. Generally, the cation channel is blocked by extra-cellular magnesium ($Mg^{2+}$) and only opened as simultaneous depolarization through the binding of Glu or agonist. In the behavioral study, intraplantar injection of specific agonist of NMDA receptors leads to mechanical hyperlgesia and inflammation that can also be antagonized by proper antagonists of NMDA receptors. Accordingly, peripheral treatments of NMDA receptor antagonists have shown to be able to attenuate or block the nociception behaviors in several animal inflammatory pain models.

In clinical medicine, pain induced by skin injuries, like burn or scald, is very complex and intolerable especially as the area of injuries are large or deep into dermis. Generally, serious skin damages may result in wide-ranged exposure of nerve endings, which may induce the release of an extensive amount of peripheral neurotransmitter to activate GluRs, and finally turn on the mechanism of inflammatory pain on skin. In this situation, the burn area of patients may become more sensitive to any mechanical stimuli, which defined as hyperalgesia. Therefore, it may bring miserable pain to most clinical burn patients undergoing therapeutic treatments, such as wound debridement, medication, rehabilitation, as well as skin graft.

In traditional treatment, NMDA receptor antagonists (ketamine e.g.), gabapentin and meperidine, are generally applied on clinical burn patients as analgesic drugs. The NMDA receptor antagonists bind to the antagonist binding site of NMDA receptors to inhibit the membrane depolarization of NMDA receptors and subsequently inhibit the stimulation of neuron cell in order to relieve the symptom of hyperalgesia in skin. However, due to blocking of NMDA receptor in central nervous system, NMDA receptor antagonists may produce some side effects, like nausea, lethargy, faint and motor uncoordination. Furthermore, the effect of the NMDA receptor antagonists is short and poor efficient so that a higher dosage or more frequent medication (such as ketamine, gabapentin and meperidine) may be needed for persistently maintaining the analgesic effect. In this way, more patients are highly risky to be addicted to the medication that used for pain relief after a long-term of chronic pain treatment.

In summary, the uses of the traditional analgesic drugs for chronic pain such as burn pain patients are limited by less efficiency, side effects and risk of drug addiction in clinical utilization. To most burn patients, it is an unbearable problem of suffering from persistently intolerable skin pain, followed by drug addition and psychological distress. Hence, it is a crucial need of developing a new strategy of relieving pain, in order to improve the poor situation of clinical chronic pain and burn pain patients, also the quality of clinical medicine.

SUMMARY OF THE INVENTION

The primary objective of this invention is to provide a small interfering RNA for gene knockdown of the N-methyl-D-aspartate receptor NR1 subunit, which can inhibit the genetic expression of NMDA receptor NR1 subunit, a pain related gene.

The secondary objective of this invention is to provide a method to inactivate the pain related gene in hypoderm, using the small interfering RNA interfere with the normal effects of the pain related gene in hypoderm, also avoid any side effects of central nervous system involved in.

Another objective of this invention is to provide a use of the small interfering RNA on pharmaceutics, using the small interfering RNA manufacture into new analgesic drugs so that the intolerable skin inflammatory pain of clinical burn patients are relieved.

Another objective of this invention is to provide a medication for relieving skin inflammatory pain, which has high efficiency and persistent effect on pain relief.

A small interfering RNA comprises 21 to 25 ribonucleic acids which are homologous to the RNA sequence of N-methyl-D-aspartate receptor NR1 for gene knockdown of N-methyl-D-aspartate receptor NR1 subunit. A method of using the small interfering RNA, applying the small interfering RNA on subcutaneous tissues for temporary interfere with the genetic expression of the NMDA receptor NR1 in subcutaneous tissues. A use of the small interfering RNA on pharmaceutics, applying the small interfering RNA on manufacture into new analgesic drugs for relieving the inflammatory pain or intolerable chronic pain, especially on clinical chronic pain and burn pain patients. An analgesic drug for skin inflammation pain comprising: the small interfering RNA and a small interfering acceptable vehicle.

Further scope of the applicability of the present invention will become apparent from the detailed description given hereinafter. However, it should be understood that the detailed description and specific examples, while indicating preferable embodiments of the invention, are given by way of illustration only, since various will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

In the various figures of the drawings, the same numerals designate the same or similar parts.

DETAILED DESCRIPTION OF THE INVENTION

Figure 1A:
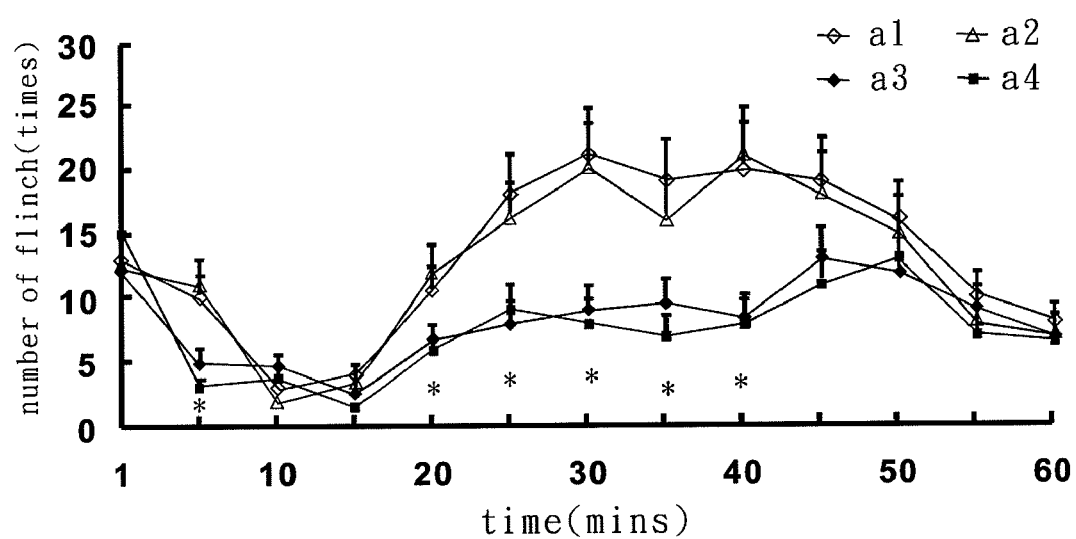
FIG. 1a is a line chart illustrating the frequency of flinches in rats on formalin-induced nociception (in the test of different sequence of small interfering RNA (siRNAs))

The present invention is tended to provide a small interfering RNA (siRNA) for gene knockdown of NMDA receptor NR1 subunit, which comprises homologous RNA sequence of NMDA receptor NR1 subunit, for specific targeting and inhibiting the normal effects of NMDA receptor NR1 subunit. Furthermore, with the utilization of the siRNA on subcutaneous tissues in creatures develops a temporary inactivation of NMDA receptor NR1 subunit in hypoderm for interfering with the normal genetic expression and functions of NMDA receptor NR1 subunit.

The principle of the present invention is based on specifically gene knockdown by RNA interference which referring to a phenomenon of post-transcriptional gene silencing only found in high eukaryotes, like *drosophila* and nematode. RNA interference is an evolutionarily gene silencing mechanism mediated by small double-stranded RNA (also called small interfering RNA or siRNA).

Since siRNA first discovery in 1990, it has been well developed as a powerful technique for functional investigation of target protein or gene. There has been reported that siRNAs in mammalian cells show to be produced through RNA processing enzyme complex (named Dicer) for converting a long dsRNA or complementary mRNAs into siRNAs. As a result, the expressed protein encoded by a gene with homologous nucleotide sequence to siRNAs will be down regulated. In this way, siRNAs are capable of transiently inactivating a gene for interest, such as a functional gene in nociception effects, with a more specific and effective manner of genetic inactivation.

As described above, NMDA receptor NR1 siRNAs are designed basing on NMDA receptor NR1 subunit gene of a biological creature, therefore, the NMDA receptor NR1 siRNAs can specifically inhibit the post-transcriptional expression of NMDA receptor NR1 subunit, as well as the normal function of NMDA receptor NR1 subunit in the biological creature.

As an example, siRNAs named NR1-1, NR1-2 and NR1-3 were synthesized using a Silencer siRNA Construction Kit (Ambion, Austin, Tex.), with homologous sequence of NMDA receptor NR1 subunit in rats (Obtained from GenBank, with accession number of U11418, 2957 base pair in length). Accordingly, the NR1-1 siRNA, NR1-2 siRNA and NR1-3 siRNA, both in 21 ribonucleotides length, were designed to target to the genetic sequence from $278^{th}$ to $298^{th}$, $512^{th}$ to $532^{nd}$ and $957^{th}$ to $977^{th}$ nucleotide of NR1 individually. (See table 1)

TABLE 1

The NMDA receptor NR1 siRNAs in the present invention

NR1-1 siRNA 5'-ACCAGGCCAAUAAGCGACAUU-3' (SEQ ID NO: 1)
3'-UUGGUCCGGUUAUUCGCUGU-5' (SEQ ID NO: 2)

NR1-2 siRNA 5'-UGUCCAUCUACUCUGACAAUU-3' (SEQ ID NO: 3)
3'-UUACAGGUAGAUGAGACUGUU-5' (SEQ ID NO: 4)

NR1-3 siRNA 5'-UGGCAAGAAUGAGUCAGCCUU-3' (SEQ ID NO: 5)
3'-UUACCGUUCUUACUCAGUCGG-5' (SEQ ID NO: 6)

For further evaluating the inactivation of the NMDA receptor NR1 siRNAs to NR1 gene, the NR1-1 siRNA, NR1-2 siRNA and NR1-3 siRNA were applied to an animal model system, in order to study the pain response of the animal model system under formalin-induced nociception (with formalin stimulation test) and Complete Freund's adjuvant (CFA)-induced nociception (with CFA stimulation test), also the post-transcriptional gene silencing of NR1. In the present invention, 1 nmole of the NR1-1, NR1-2 and NR1-3 siRNA were co-injected with 2 μL of polyethyleneimine (PEI) for well delivering into cells of the animal model system.

Formalin Stimulation Test

Formalin is an irritative chemical, especially to eyes, mucosa membrane and skin, which may cause hypersensitivity reaction on skin. It is suggested that the formalin stimulation test is the most frequently used model system for assessing the efficacy of anti-hypersensitivity ability elicited by NMDA receptor antagonists. Generally, the immediate response to formalin, defined as phase 1, also called acute phase, reflects the activation of primary afferent nociceptors. The later response, defined as phase 2, also called tonic phase, reflects a continuing stimulation of peripheral nociceptors and central sensitization triggered by the phase 1 neurotransmission input from the periphery. Two phase of afferent input evokes mass release of excitatory transmitter, Glu for example, initiating pain chronification and inflammation on model animals.

As example, Sprangue-Dawley rats (SD rats), 250 to 350 g in weight, were prepared and housed in a lab environment for 3 assays of effects of siRNA followed by the formalin stimulation test: (a) test of different sequence of siRNAs, (b) test of dosage of siRNA and (c) test of time course of siRNA. The SD rats were fed a standard laboratory diet and tap water, kept at 23±1° C. with a 12 hours light/dark cycle, all following the guidelines of animal pain research.

(a) Test of different sequence of siRNAs: as shown in table 2, the SD rats were randomly assigned to 4 groups including a vehicle group (a1) to serve as a control, and three different groups of NR1-3, NR1-2, NR1-1 siRNA (a2, a3 and a4). The first injection was administered 3 days before a formalin assay in each group, with 2 μL of polyethyleneimine (PEI) in control group (a1) and 1 nmole of NR1-3, NR1-2 and NR1-1 siRNA in a2, a3, a4 group individually. To exclude the possible systemic effects on SD rats, the first injection was applied on one paw of SD rats, following by secondary injection of 1% formalin on the contralateral paw 3 days later. The skin tissues of SD rats in 4 groups were dissected immediately after the formalin injection for NR1 analysis by using real-time polymerase chain reaction (Rt-PCR) and western blotting.

TABLE 2

Groups assignment in the test of different sequence of siRNAs

| groups | First injection | | Second injection | |
| --- | --- | --- | --- | --- |
| | agents | dosage | agents | dosage |
| a1 (control) | polyethyleneimine | 2(μL) | 1% formalin | 50(μL) |
| a2 | NR1-3 siRNA | 1(nmole) | 1% formalin | 50(μL) |
| a3 | NR1-2 siRNA | 1(nmole) | 1% formalin | 50(μL) |
| a4 | NR1-1 siRNA | 1(nmole) | 1% formalin | 50(μL) |

Referring to FIG. 1a summarizes the formalin-induced flinching response after formalin injection in a1 to a4 groups, wherein 2 phases of nociceptive behavioral patterns are shown. After subcutaneous injections of 1% formalin, the first phase (acute phase) of nociception begins immediately and lasts for 3 to 5 minutes, following by a period of 10 to 15 minutes with very mild response. The second phase (tonic phase) of nociception starts at approximately 15 to 20 minutes later than formalin injection and lasts for 20 to 40 minutes. In control group, the frequency of flinch is around 12 to 13 times/per min in first phase but fast decrease to 5 times/per min in 5 minutes. In additional, the frequency of flinch goes up to 20 times/per min in the second phase at around 20 minutes. In contrast, except the SD rats in the a2 group shows similar frequency of flinch to the control group, the frequency of flinch in a3 and a4 group are significant diminished both in first and second phase, with only 4 to 6 times/per min in first phase and 8 to 12 times/per min in second phase. As a result, the number of flinches will dramatically decrease at the 5 minutes, also during the period of 20-40 minutes in SD rats that received intra-dermal injection of 1 nmole NR1-1 and NR1-2 siRNA compared with SD rats that received intra-dermal injection of 2 μL PEI.

To examine the effect of siRNA on gene expression, real time PCR and western blotting were used for analysis of gene expression of NMDA receptor subunits and interferon. The RNA samples of 4 groups of SD rats were isolated and purified from skin using Total RNA Mini Kit (Geneaid Biotech Ltd, Sijhih City, Taiwan). Moreover, the complementary DNA sample of 4 groups was performed by reverse transcription using random primers and High Capacity Complementary DNA Reverse Transcription Kit (Applied Biosystems Inc, Foster City, Calif.) to obtain cDNA samples. Using ABI Prism 7500 Sequence Detection System (Applied Biosystems, Foster City, Calif.) and SYBR Green detection, real-time PCR was performed in a two-step reaction with the following PCR program: stage 1, 50° C. for 3 min; stage 2, 95° C. for 10 min; stage 3, with 50 cycles, each consisting of 15 sec at 95° C. and 45 sec at 60° C. For real-time PCR, 12.5 μL, of 2× SYBR Green PCR Master Mix (ABI, Foster City, Calif.) and 1.0 μL of the desired primer mixture (10μ mole) were added to the cDNA samples to reach a final volume of 25 μL, The PCR setup was singleplex, where the target and reference genes were detected in separate tubes. In order to excluded the inactivation on NR2 subunits and induction of interferon response, the mRNA level of both NR1 and NR2 subunits of the NMDA receptor, also interferon were analyzed in Rt-PCR program. (In table 3 summarize the primer designs for NR1, NR2 and interferon in Rt-PCR program)

TABLE 3 primer designs for NR1, NR2 and interferon

| Target | | primers |
|---|---|---|
| NR1 | Fwd. | 5'-GCG ACT CCC GCA GCA AT-3' (SEQ ID NO: 9) |
| | Rev. | 5'-CCC CTG CCA TGT TCT CAA AA-3' (SEQ ID NO: 10) |
| NR2A | Fwd. | 5'-TCC ACT CAA GGA ATC TTG TGA GAT AT-3' (SEQ ID NO: 11) |
| | Rev. | 5'-ACT TGC CCA TGT GTA TTT ATT TGT TT-3' (SEQ ID NO: 12) |
| NR2B | Fwd. | 5'-AAC CCT CGT GGC CGA CA-3' (SEQ ID NO: 13) |
| | Rev. | 5'-GGT GGA CAG ATG CGG GAA-3' (SEQ ID NO: 14) |
| NR2C | Fwd. | 5'-GGC CCA GCT TTT GAC CTT AGT-3' (SEQ ID NO: 15) |
| | Rev. | 5'-CCT GTG ACC ACC GCA AGA G-3' (SEQ ID NO: 16) |
| NR2D | Fwd. | 5'-AGG GTT TCT GCA TTG CCC CAT T-3' (SEQ ID NO: 17) |
| | Rev. | 5'-TCA CCA ATC ATG CCA TTC CA-3' (SEQ ID NO: 18) |
| α-inter-feron | Fwd. | 5'-CTT GGC TGT TTG CCC CAT T-3' (SEQ ID NO: 19) |
| | Rev. | 5'-CGT GAC AGT AGC TGC GGT TCC-3' (SEQ ID NO: 20) |

Figure 1B:
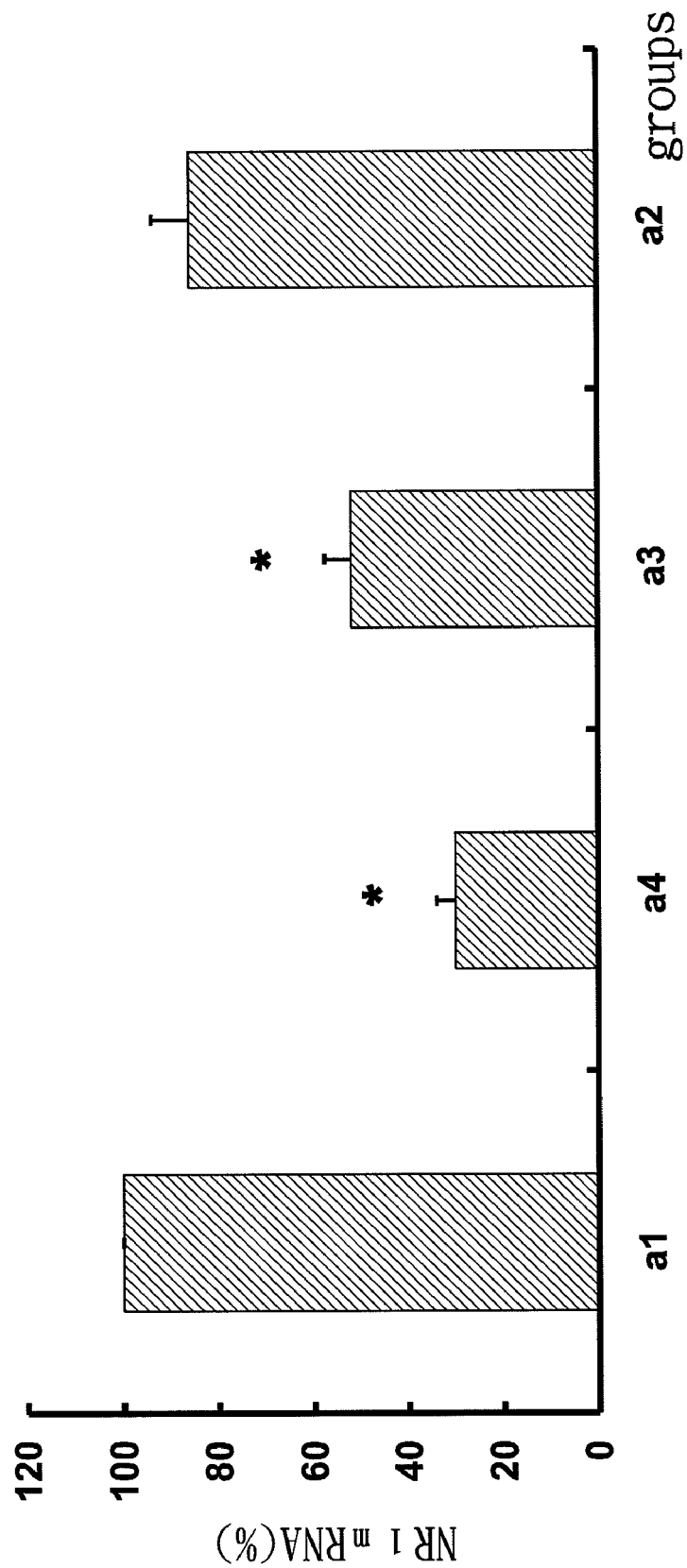
FIG. 1b is a diagram illustrating the mRNA expression level of NR1 in rats' skin tissue (in the test of different sequence of siRNAs)
Figure 1C:
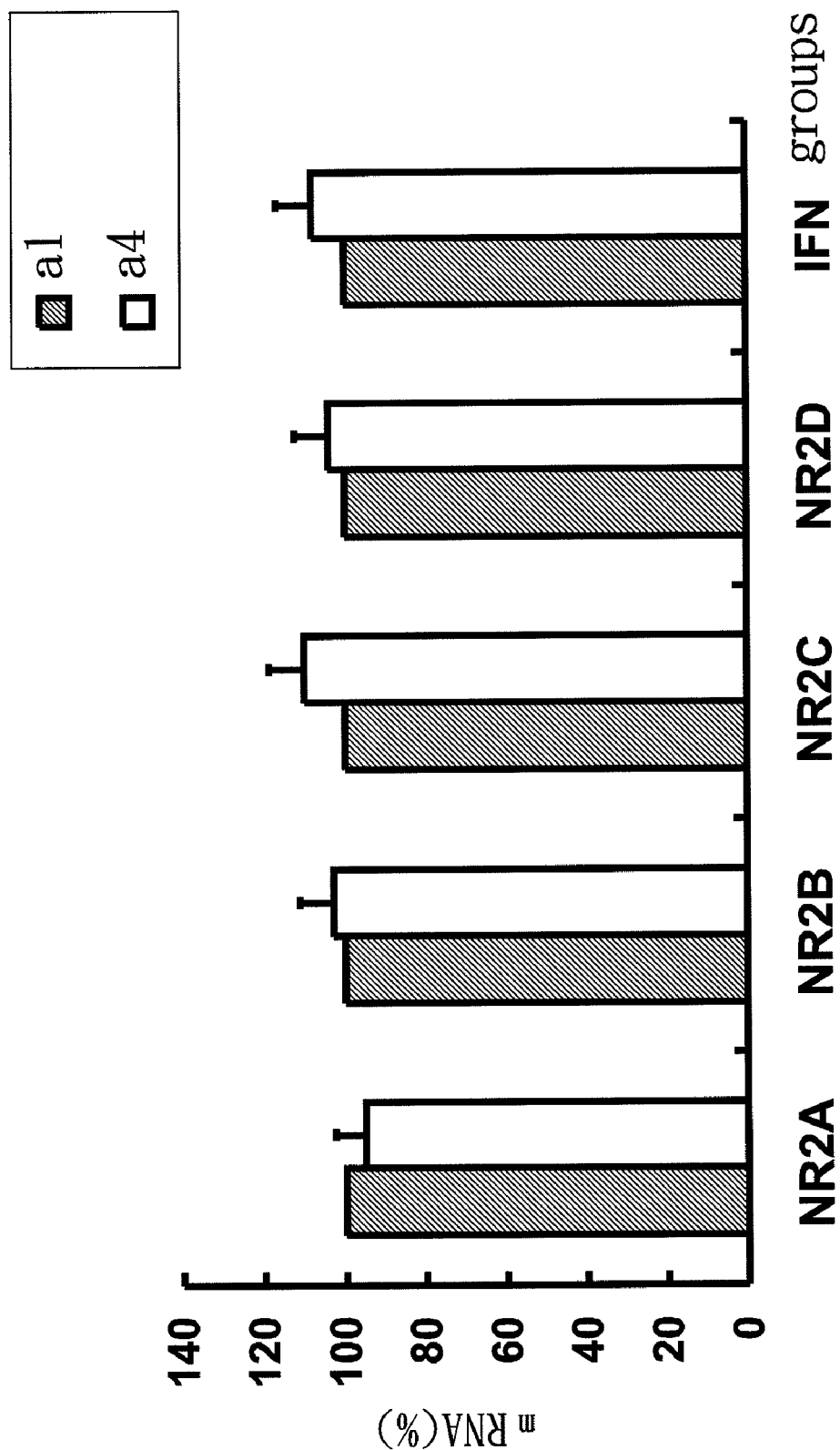
FIG. 1c is a diagram illustrating the mRNA expression level of NR2 and interferon in rats' skin tissue (in the test of different sequence of siRNAs)

Referring to FIGS. 1b and 1c, illustrates NR1, NR2 and interferon gene expression of skin tissues in 4 groups of SD rats, wherein, the FIG. 1c only disclose the gene expression level of SD rats in group a1 and a4. It has been shown that the mRNA level of NR1 is significant lower in NR1-1 siRNA or NR1-2 siRNA delivering SD rats (group a3 and a4) than that in the control group. Compare to the mRNA expression level of NR1 in the control group (defined as 100%), the decrease of NR1 mRNA in the a4 group (around 70% decreases) is greater than that in a3 (about 55%) and a2 groups (about 10%). Furthermore, the NR1-1 siRNA treatment does not interfere with the mRNA level of other formalin-induced nociception related subunits including NR2A, NR2B and NR2C, or non-related subunit NR2D. Also, there is no obvious difference noted in mRNA level of interferon-α between a1 and a4 groups.

On the other hand, total proteins samples from skin tissues were prepared by additional 1:20 dilution of T-PER Tissue Protein Extraction Reagent (PIERCE., Rockford, Ill.) containing 25 mM bicine, 150 mM sodium chloride (pH 7.6), protease inhibitors, 100 mM 4-(2-Aminoethyl)benzenesulfonyl fluoride hydrochloride, 80 M aprotinin, Crystalline, 5 mM Bestatin, 1.5 mM E-64, Protease inhibitor, 2M leupeptin and 1 mM pepstatin A. The protein samples were homogenized with a homogenizer. After being placed on ice for 30 min, the homogenized protein samples were centrifuged at 12,000 rpm/min for 30 min at 4° C. The supernatant (total protein samples) was collected and assayed for protein content using the Quant-iT™ Protein Assay Kit (Invitrogen, Carlsbad, Calif.). The total protein samples (30 μg) were electrophoresed on a 10% sodium dodecylsulfate-polyacrylamide gel as suggested by the manufacturer. After electrophoresis, the analysis data were transferred to a polyvinylidine fluoride membrane and blocked with 5% nonfat dry milk. The primary antibody (1:2000 dilution of rabbit polyclonal anti-glutamate receptor NR1; Sigma) and the secondary antibody (1:5000 dilution of horseradish peroxidase-coupled goat anti-rabbit immunoglobulin G; Chemicon, Billerica, Mass.) was sequentially added and allowed to incubate at suitable temperature (4° C. or room temperature) in fresh blocking buffer. Finally, the secondary antibodies were detected by Western Blot Chemiluminescence Reagent Plus (Millipore, Billerica, Mass.) to obtain western blot data. For densitometry analyses, the western blot data were scanned and quantified with Image-Pro® Plus Analysis Software (MediaCybernetics, Silver Spring, Md.), also expressed as a immunoreactivity ratio of NR1 to β-tubulin (a normally expressed protein in rats).

Figure 1D:
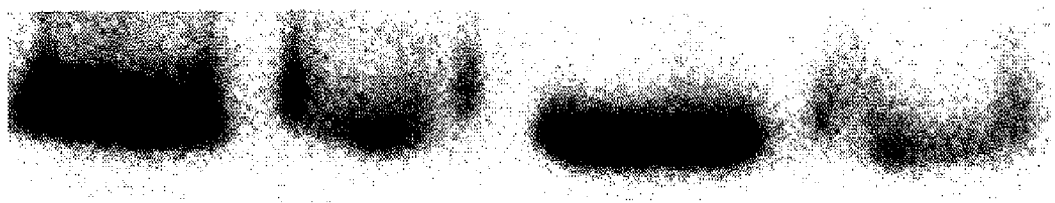
FIG. 1d is a western blot of the protein expression of NR1 in rats' skin tissue (in the test of different sequence of siRNAs)
Figure 1E:
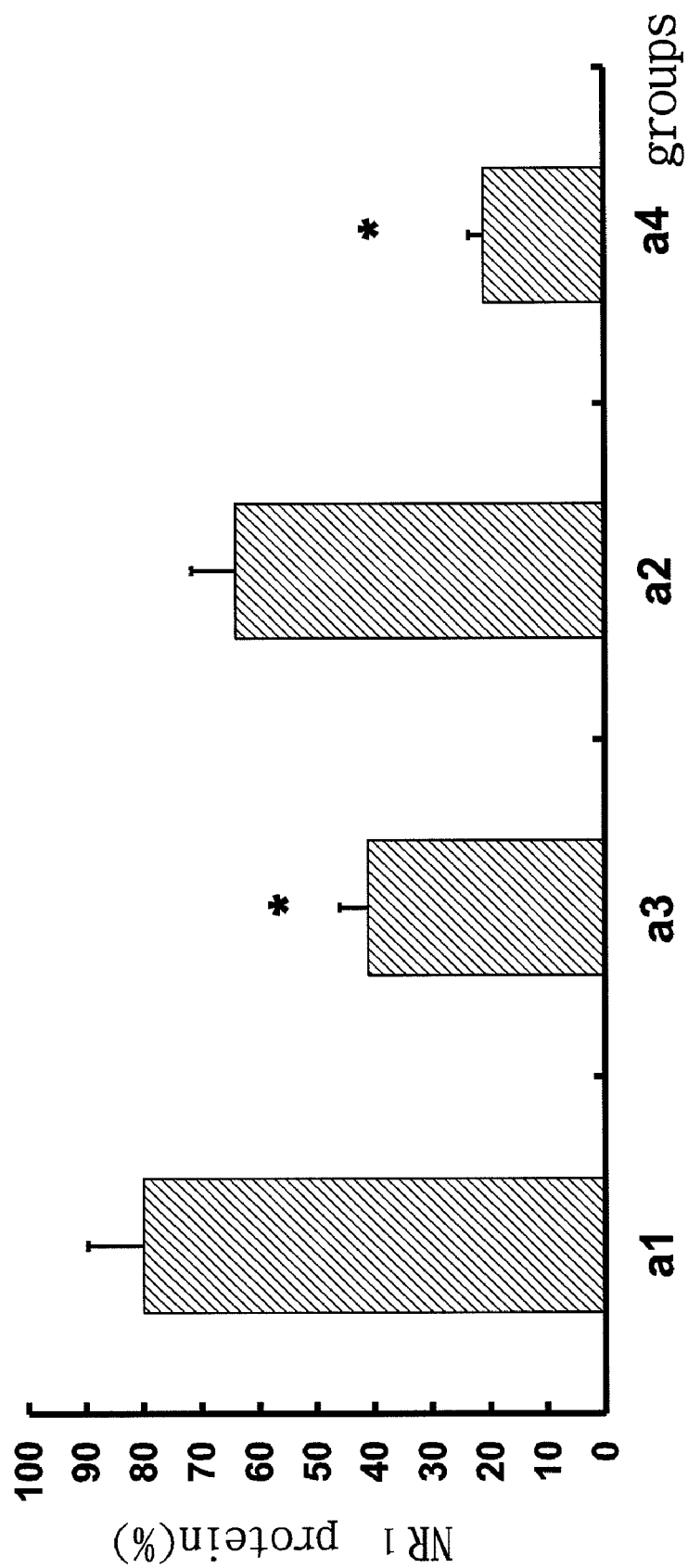
FIG. 1e is a diagram illustrating the protein expression level of NR1 in rats' skin tissue (in the test of different sequence of siRNAs)

Referring to the FIGS. 1d and 1e illustrates the protein expression of skin in 4 groups of SD rats, wherein the FIG. 1d shows the photograph of western blot data, and the FIG. 1e shows the immunoreactivity ratio of NR1 to β-tubulin in 4 groups. It has been shown that the protein level of NR1 is obviously lower in group a3 and a4 SD rats which have undergone the NR1-1 siRNA or NR1-2 siRNA treatment than that in the control group. Additionally, the group a4 and a3 show the less immunoreactivity ratio (around 22% and 40%) of NR1 to β-tubulin among other groups (a1 with the highest ratio of 80% and a2 with 65%). Thus, it is evidenced that the NR1-1, NR1-2 and NR1-3 siRNA delivery can significant decrease the NR1 gene expression both in mRNA and protein levels, especially for NR1-1 siRNA.

As described in (a) test of different sequence of siRNAs, it is suggested that the NMDA receptor NR1 siRNAs in the present invention do have gene silencing effects on NR1, therefore, the mRNA expression of NR1, protein expression of NR1, as well as the NR1 involved nociception which induced by any irritant are specifically interrupted. Furthermore, the inactivation of the NMDA receptor NR1 siRNAs is specific to NR1 gene but other formalin-inducing nociception related NMDA receptor subunits (NR2A for example) or interferon.

(b) Test of dosage of siRNA: as shown in table 4, the SD rats were randomly assigned to 6 different groups including a PEI group (b1), a saline group (b2) and a mismatched (MM)-NR1-1 siRNA group (b3) served as a positive or negative control, also three groups of NR1-1 siRNA with diverse dose (b4, b5 and b6). Based on the procedure in (a) test of different siRNA, the first injection was also administered 3 days before the formalin assay of each group, with 2 μL of PEI, 100 μL of saline, 1 nmole of MM-NR1-1 siRNA and 0.5, 1, 2 nmole of NR1-1 siRNA treatment in b1,b2,b3,b4,b5 and b6 individually. To exclude the possible systemic effects on SD rats, the first injection was applied on one paw of the SD rats, followed by second injection of 1% formalin on the contralateral paw 3 days later. The skin tissues of SD rats in 6 groups were dissected immediately after the formalin injection in each rat for NR1 analysis by using real-time polymerase chain reaction (Rt-PCR) and western blotting.

TABLE 4

Groups assignment in the test of dosage of siRNA

| | First injection | | Second injection | |
|---|---|---|---|---|
| groups | agents | dosage | agents | dosage |
| b1 (control) | PEI | 2(μL) | 1% formalin | 50(μL) |
| b2 (control) | saline | 100(μL) | 1% formalin | 50(μL) |
| b3 (control) | MM-NR1-1 siRNA[a] | 1(nmole) | 1% formalin | 50(μL) |

TABLE 4-continued

Groups assignment in the test of dosage of siRNA

| groups | First injection | | Second injection | |
|---|---|---|---|---|
| | agents | dosage | agents | dosage |
| b4 | NR1-1 siRNA | 0.5(nmole) | 1% formalin | 50(μL) |
| b5 | NR1-1 siRNA | 1(nmole) | 1% formalin | 50(μL) |
| b6 | NR1-1 siRNA | 2(nmole) | 1% formalin | 50(μL) |

[a]The mismatched (MM)-NR1-1 siRNA injected into b3 is a mismatched NR1-1 siRNA without meaningful homology to any known rat's genetic sequence which obtained from Ambion. The sequence of MM-NR1-1 siRNA is shown in Table 5.

TABLE 5

The sequence of mismatched (MM)-NR1-1 siRNA (SEQ ID NO: 7)
MM-NR1-1 siRNA 5'-ACCAGCGCAAAAACGGACATT-3'
(SEQ ID NO: 8)
3'-TTUGGUCGCGUUUUUGCCUGU-5'

Figure 2A:
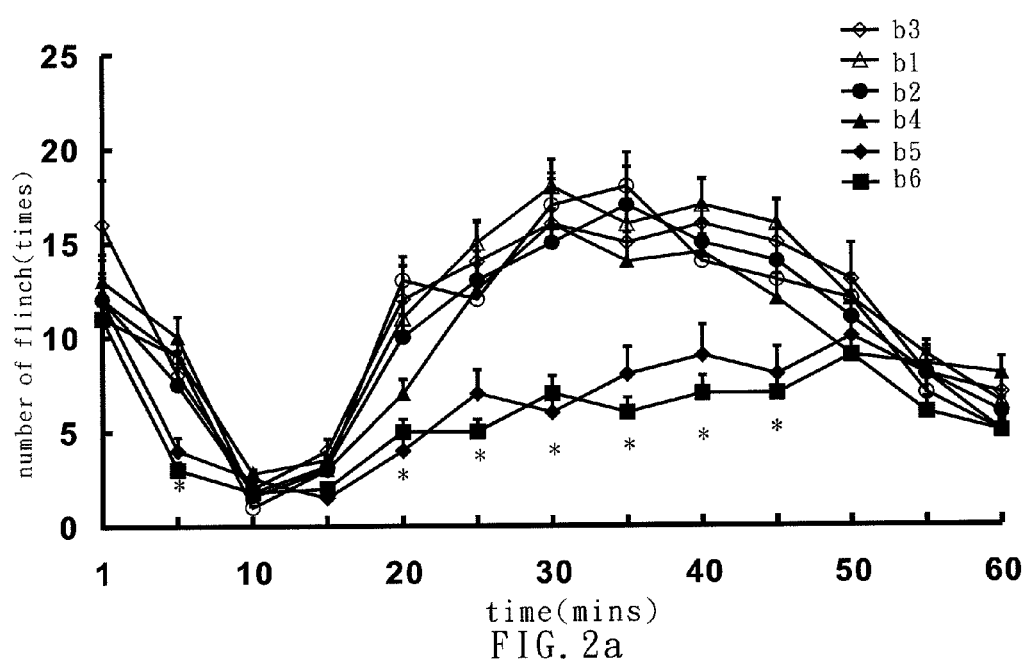
FIG. 2a is a line chart illustrating the frequency of flinches in rats on formalin-induced nociception (in the test of dosage of siRNA)

Referring to the FIG. 2a, summarizes the formalin-induced flinching response after formalin injection in b1 to b6 groups, wherein shows the 2 phase of nociceptive behavioral patterns in formalin assay. In the dosage study of siRNA, the frequency of flinch was decreased at 5 minutes and during the period of 20-45 minutes in SD rats after administration of 1 nmole (b5) and 2 nmole (b6) (about 3 to 5 times/per min in the first phase, and 4 to 8 times/per min in the second phase), but not 0.5 nmole NR1-1 siRNA compared with control groups (b1, b2 and b3) that received intra-dermal injection of 2 μL, PEI, 1 nmole MM-NR1-1 siRNA or 100 μL saline. As a result, the decrease of flinch frequency of NR1-1 siRNA treated SD rats in formalin assay shows dose-depended manner on delivery of NR1-1 siRNA. Also, as no significant anti-nociceptive effects have been noted on the paw of rats which is contralateral to the paw received intra-dermal injection of formalin injected with NR1-1 siRNA. It is indicated that the anti-nociceptive effect of NR1-1 siRNA is not resulted from a systemic effect, but from local effect of NR1-1 siRNA.

According to the protocol described above [In the (a) test of different sequence of siRNAs], the RNA and protein samples of 6 groups (b1 to b6) of SD rats were isolated and purified from skin tissues for examining the effect of siRNA on gene expression (including mRNA level and protein level) of NR1 by real time PCR and western blotting.

Figure 2B:
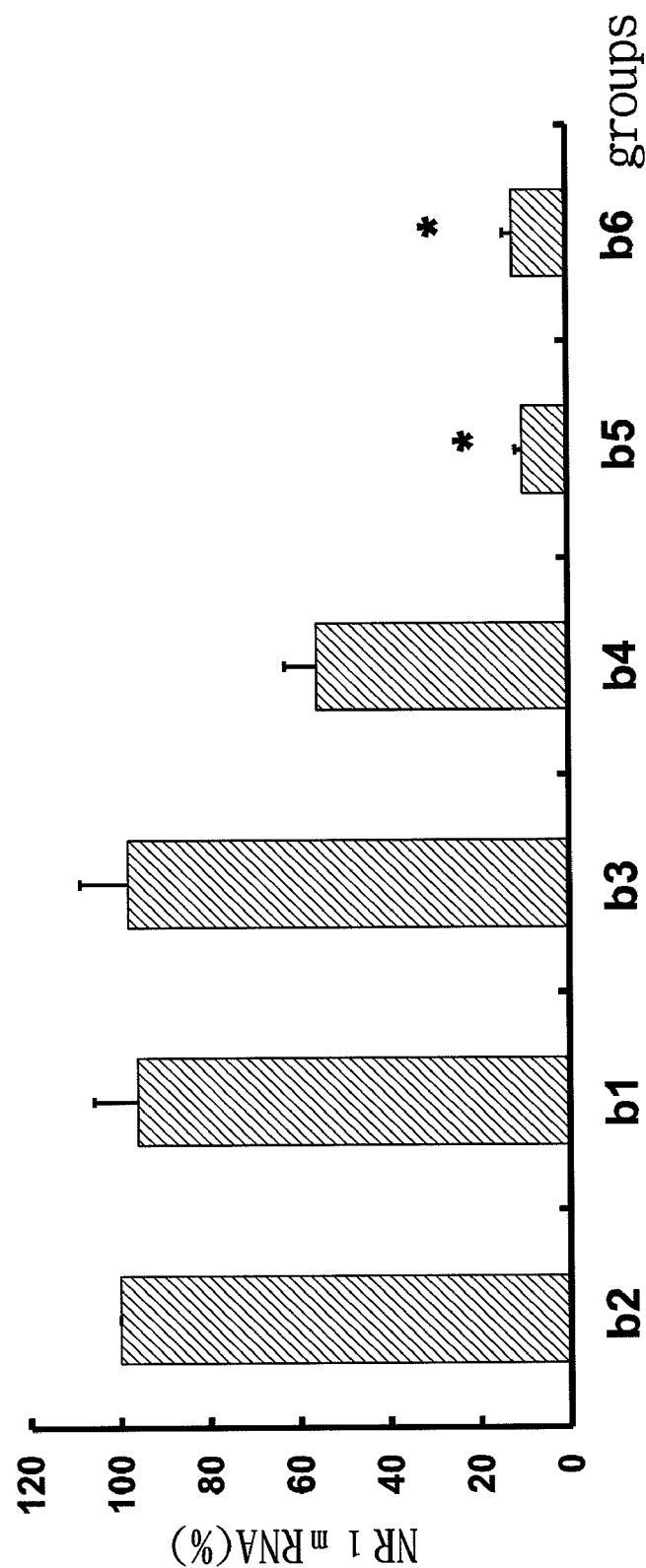
FIG. 2b is a diagram illustrating the mRNA expression level of NR1 in rats' skin tissue (in the test of dosage of siRNA)

Referring to FIG. 2b illustrates NR1 mRNA expression of skin in 6 groups of SD rats in the test of dosage, wherein shows no obvious differences in mRNA level of expression demonstrated by Rt-PCR between two doses of 1 nmole and 2 nmole NR1-1 siRNAs. It revealed that the mRNA level of NR1 is significant lower in 1 nmole and 2 nmole NR1-1 siRNA treated SD rats (b5 and b6), than that in the control groups (b1, b2 and b3) and even in 0.5 nmole NR1-1 siRNA treated rats (b4). Compare to the expression level of NR1 mRNA in the b1 groups (defined as 100%) the decrease of NR1 mRNA in the b4, b5 and b6 group reveals a clear dose-dependent manner, with around 50%, 90% and 89% lost individually.

Figure 2C:
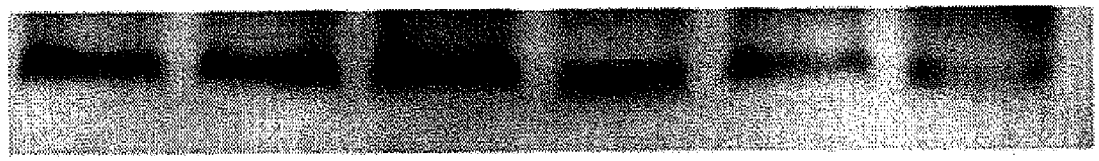
FIG. 2c is a western blot photograph of the protein expression of NR1 rats' skin tissue (in the test of dosage of siRNA)
Figure 2D:
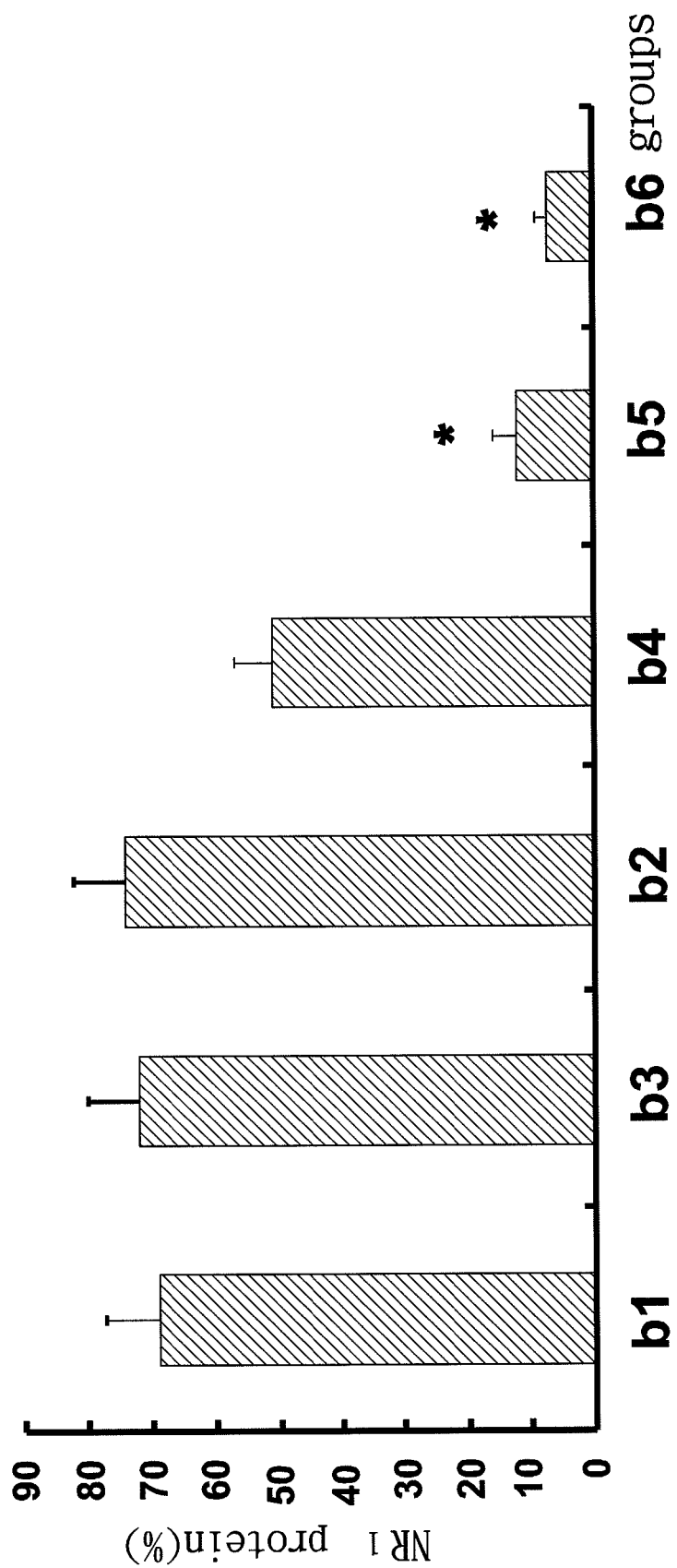
FIG. 2d is a diagram illustrating the protein expression level of NR1 in rats' skin tissue (in the test of dosage of siRNA)

Furthermore, referring to FIGS. 2c and 2d, illustrates NR1 protein expression of skin in 6 groups of SD rats, wherein, the FIG. 2c shows the photograph of western blot data, and the FIG. 2d shows the immunoreactivity ratio of NR1 to β-tubulin of 6 groups in the test of dosage. It is revealed that the protein level of NR1 significantly decreased in rats with NR1-1 siRNA treatment, especially with injection of higher dose like 1 nmole or 2 nmole. Moreover, the group b5 and b6 show significant less immunoreactivity ratio of NR1 to β-tubulin than other groups, with approximately rate of 85% and 90% inhibition. Hence, it have been proved that the decrease of NR1 protein level in the b4, b5 and b6 groups are mainly depending on the dose of NR1-1 siRNA delivery in rats, with a positive dose-dependant effect on inhibition of protein expression.

As described in (b) test of dosage of siRNA, it is believed that the inactivations of NMDA receptor NR1 siRNAs in the present invention on NR1 gene expression are localized and dose-dependant, wherein, the dose of 1 nmole shows effective interruption in formalin-induced flinch response and gene expression. Therefore, the dose of 1 nmole siRNA has subsequent used for further examination of time course study in the present invention.

(c) Test of time course of siRNA: as shown in table 6, in which randomly assigned SD rats into 8 groups including 3, 7, 14 and 21-days vehicle groups of 2 μL PEI injected at each time periods, and 3, 7, 14 and 21-days recovery groups of 1 nmole NR1-1 injected at each time periods. In the time course study, the vehicle groups (c1, c2, c3 and c4) were served as the controls in the formalin assay and gene expression. Similar to the procedural in the (a) test of different sequence of siRNAs and (b) test of dosage of siRNA, skin tissues of SD rats in each group (c1 to c8) were dissected immediately after the formalin injection for analysis of NR1 expression by real-time PCR and western blotting.

TABLE 6

Group assignment in the test of time course of siRNA

| groups | First injection | | | Second injection | |
|---|---|---|---|---|---|
| | agents | time[a] | dose | agents | dose |
| c1 | PEI | 3 days | 2(μL) | 1% formalin | 50(μL) |
| c2 | PEI | 7 days | 2(μL) | 1% formalin | 50(μL) |
| c3 | PEI | 14 days | 2(μL) | 1% formalin | 50(μL) |
| c4 | PEI | 21 days | 2(μL) | 1% formalin | 50(μL) |
| c5 | NR1-1 siRNA | 3 days | 1(nmole) | 1% formalin | 50(μL) |
| c6 | NR1-1 siRNA | 7 days | 1(nmole) | 1% formalin | 50(μL) |
| c7 | NR1-1 siRNA | 14 days | 1(nmole) | 1% formalin | 50(μL) |
| c8 | NR1-1 siRNA | 21 days | 1(nmole) | 1% formalin | 50(μL) |

[a]The first injection of NR1-1 siRNA in each group was administrated 3, 7, 14, 21 days before the secondary injection of 1% formalin.

Figure 3A:
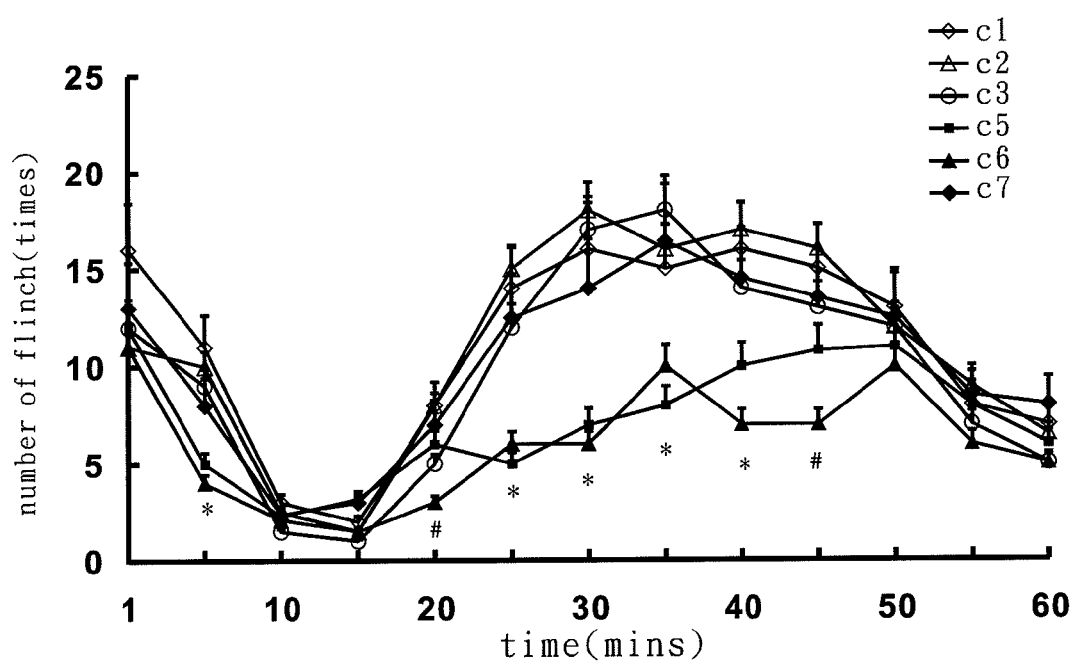
FIG. 3a is a line chart illustrating the frequency of flinches in rats on formalin-induced nociception (in the test of time course of siRNA)

Referring to the FIG. 3a, summarize the flinching response of rats of formalin assay in the time course study, wherein, the flinch number of SD rats in group c4 and c8 are excluding from it. In the time course study, the formalin assay performed on the third and seventh day after injection of 1 nmole NR1-1 siRNA (c5 and c6) shows significant lower number of flinches at 5 minutes and during the period of 25-40 minutes in formalin-stimulated nociception (with around 4 to 6 times/per min of flinch frequency). Additionally, there is another anti-nociceptive effect (decrease in the number of flinches) at 20 and 45 minutes in formalin-inducted nociception with 5 to 11 times/per min of flinches response. However, the formalin stimulation on 14 or 21—days of NR1-1 siRNA treated SD rats (c7 and c8) shows no different than that in control rats, still have high frequency of flinch response during the formalin assay.

Figure 3B:
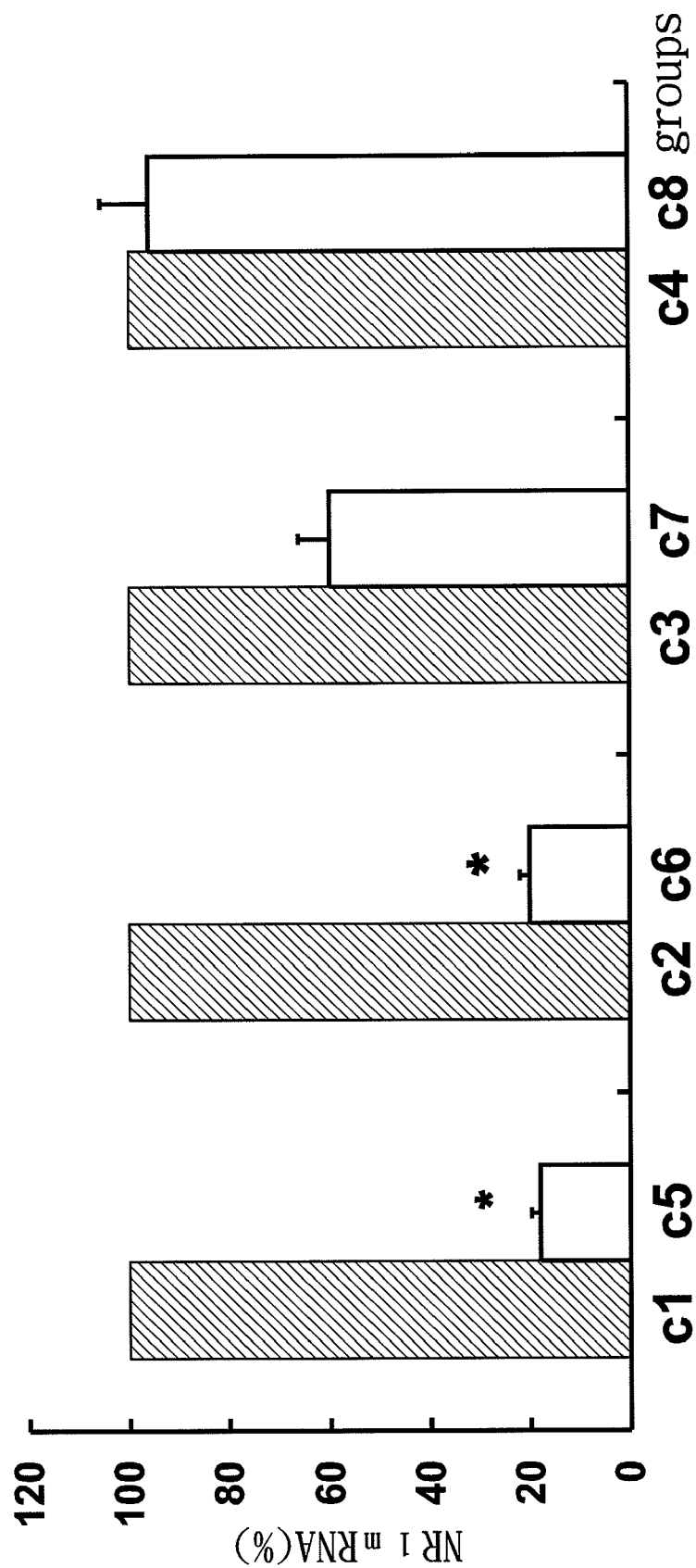
FIG. 3b is a diagram illustrating the mRNA expression level of NR1 in rats' skin tissue (in the test of time course of siRNA)

Referring to FIG. 3b illustrates NR1 mRNA expression of each SD rat in the test of time course, wherein the 3 and 7-days recovery groups of 1 nmole NR1-1 injection (c5 and c6) has significant lower mRNA expression level. On the other hand, it tends to show that the decreases of NR1 mRNA in 14 and 21-days groups (c7 and c8) recover by days.

Figure 3C:
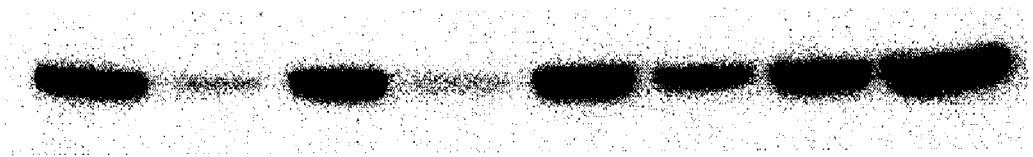
FIG. 3c is a western blot of the protein expression of NR1 in rats' skin tissue (in the test of time course of siRNA)
Figure 3D:
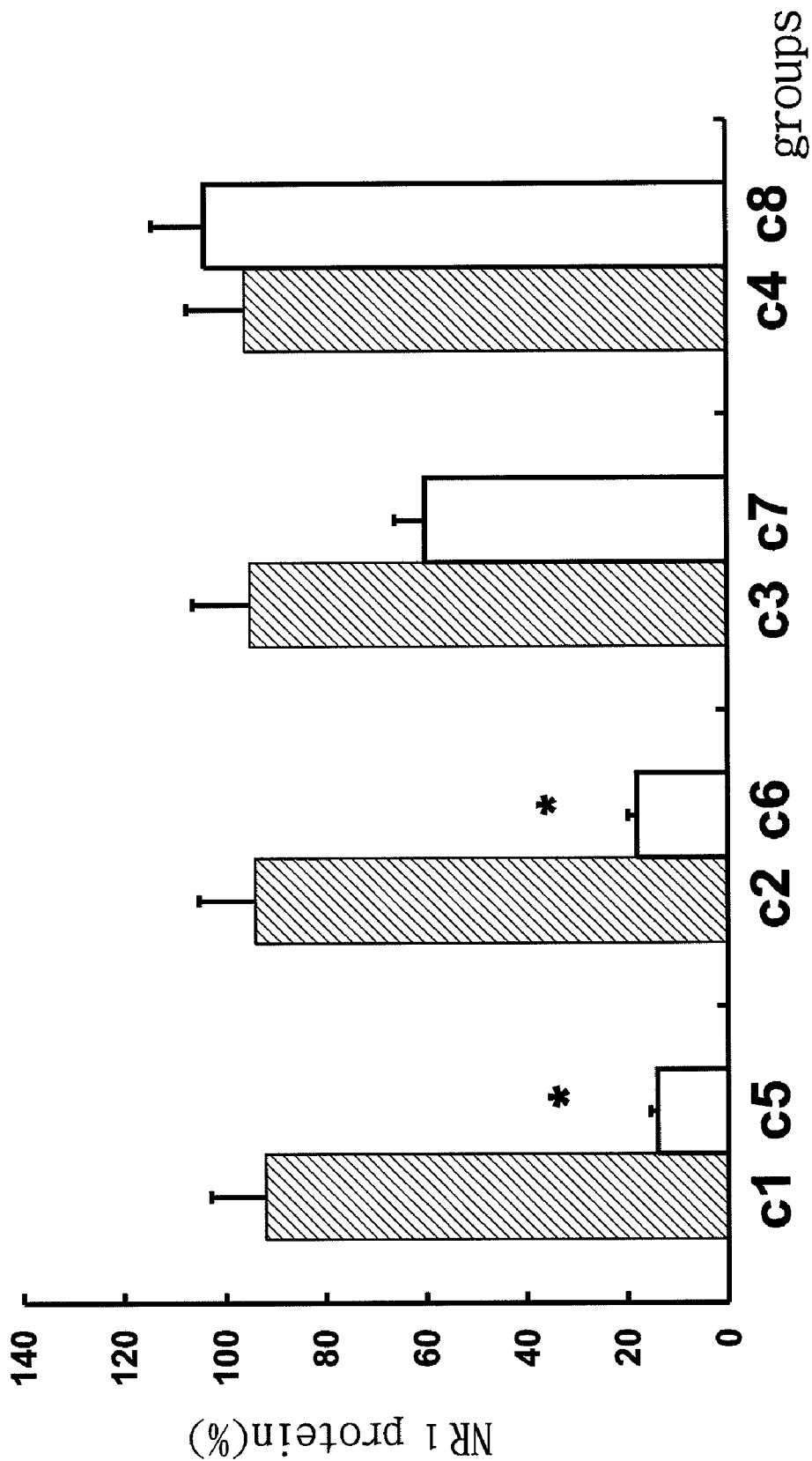
FIG. 3d is a diagram illustrating the protein expression level of NR1 in rats' skin tissue (in the test of time course of siRNA)

Referring to FIGS. 3c and 3d shows NR1 protein expression of each SD rat in the test of time course, in which the decreases of NR1 protein are correlated with the anti-nociceptive effects and decreased mRNA expression in the time course study. As a result, the inhibition of 1 nmole NR1-1 siRNA on NR1 gene expression is temporary, which will only last for 7 to 14 days.

As described in (c) test of time course of siRNA, it is believed that the gene silencing effects of NMDA receptor NR1 siRNAs in the present invention on NR1 gene are temporary, which will self-degrade by days and only last for 7 to 14 days. Therefore, it is no longer to cause any permanent disorders to NR1 gene as if the intra-dermal delivery of the NMDA receptor NR1 siRNAs has performed.

Complete Freund's Adjuvant (CFA) Stimulation Test

Complete Freund's adjuvant (CFA) is an inflammation-producing chemical used to produce long-lasting pain responses that mimic clinical pain in humans. The injection of CFA into the hind paw of rat has been shown to produce mechanical hyperalgesia accompanied by long-lasting inflammation on the injected hind paw. It has been reported that NMDA receptors play an important role in mediating the development of mechanical hyperalgesia inducing by intra-plantar CFA injection.

Rats in the CFA test were fed a standard laboratory diet and tap water, also kept at 23±1° C. with a 12 hours light/dark cycle, following the guidelines of model pain research. Moreover, all rats were habituated to a lab environment for 2 days before the mechanical hyperalgesia assay. As arranged in table 7, 4 groups (d1 to d4) of rats are well administrated for the CFA test: rats were received subcutaneous injection of CFA (0.1 mL, Sigma) two days after first subcutaneous injection of 2 µL PEI (d1), 100 µL saline, 1 nmole MM-NR1 siRNA (d3) or 1 nmole NR1-1 siRNA (d4) separately. First of all, the baseline data of 50% withdrawal threshold was recorded before any injected treatment on rats, as following, a behavior test was performed for measuring the motor function of rats after the first injection of PEI, saline and siRNAs. Next, skin tissues of each rat were dissected immediately after the CFA injection for genetic expression analysis of NR1 by Rt-PCR. Finally, the mechanical hyperalgesia assay was performed 1 day after the injection of CFA for taking the 50% withdrawal threshold again.

TABLE 7

Group assignment in the CFA stimulation test

| groups | First injection | | Second injection | |
|---|---|---|---|---|
| | agents | dose | agents | dose |
| d1 (control) | PEI | 2(µL) | CFA | 0.1(mL) |
| d2 (control) | saline | 100(µL) | CFA | 0.1(mL) |
| d3 | MM-NR1-1 siRNA | 1(nmole) | CFA | 0.1(mL) |
| d4 | NR1-1 siRNA | 1(nmole) | CFA | 0.1(mL) |

In the behavioral tests, rats in each treatment group (d1 to d4) were conducted by a blinded observer to evaluate motor coordination. At the beginning, rats were first trained in the morning before the behavioral test for keeping balance (for 30 seconds) on an Ugo Basile (Comerio, Italy) rotarod apparatus revolving at 12 rpm/per minute. However, during the behavioral test, the rats were placed on the rotarod apparatus revolving with 40 rpm/per minutes for measuring the time of rats keeping on the rolling rod.

Figure 4A:
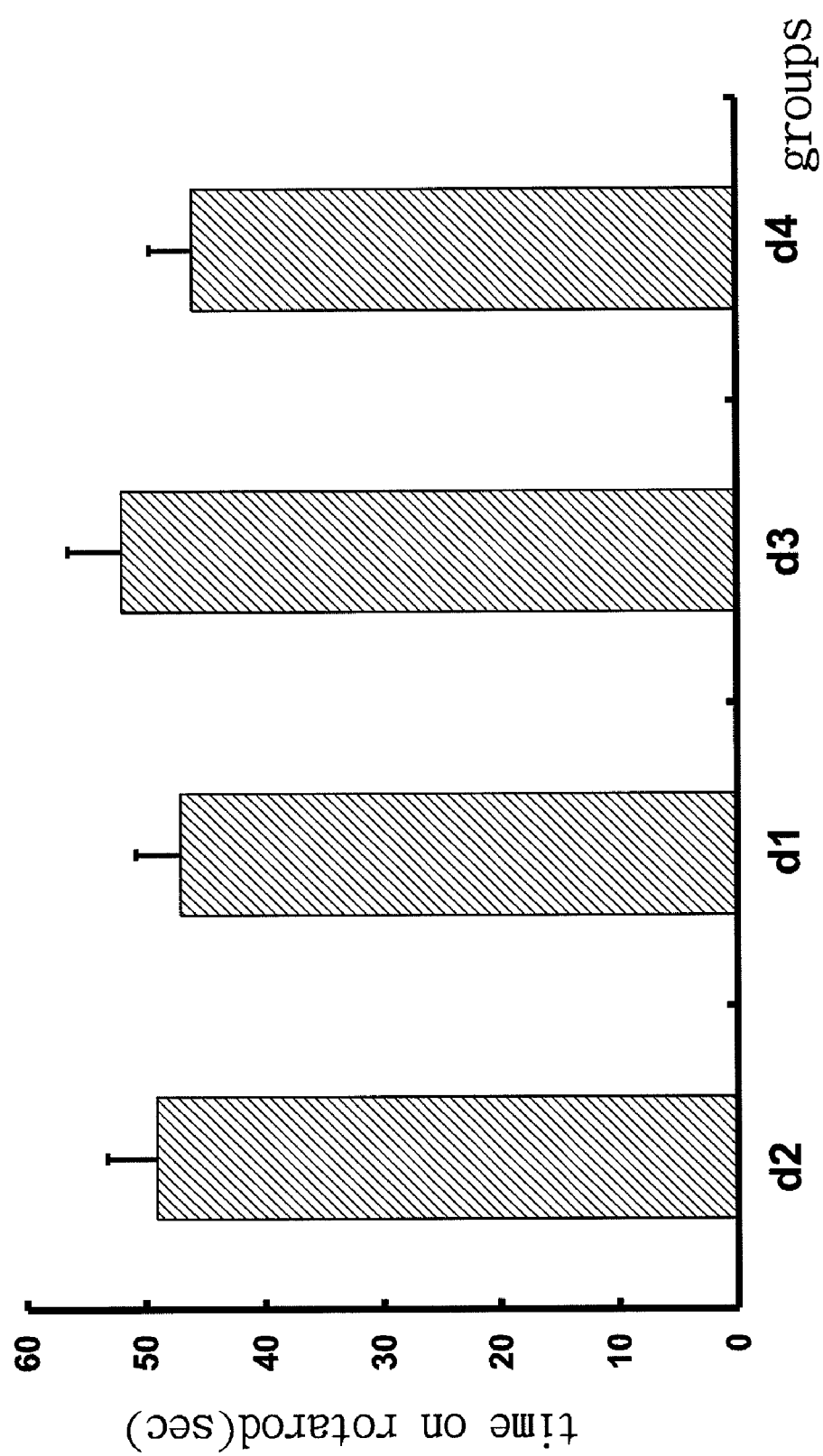
FIG. 4a is a diagram illustrating the motor coordination time of rats in rotarod test.

Referring to FIG. 4a, sums up the maintenance of rats on the rolling rod in which demonstrates the ability of balance and motor coordination of rats. It has showed that there is no difference in motor coordination in rats received intra-dermal injection of NR1-1 siRNA (d4) or MM-NR1-1 siRNA (d3) rats when compared with other rats in the vehicle treatment groups (d1 and d2). All of rats in each group have kept balance over 47 seconds on the revolving rod.

In CFA stimulation test, the CFA-induced inflammation was accomplished by injection of 0.1 ml CFA into the subcutaneous tissue of hind paw after anesthetized with 2.5% isoflurane for 2-3 minutes. In order to examine the mechanical sensitivity of rats, each group of rats were set into a plastic box (around 11×13×24 cm) on an elevated metal mesh floor, allowing for 30 min of habituation. According to a method described by Chaplan et al. in 1994, the withdrawal thresholds of mechanical paw were recorded, as the hind paw of rats suffered from one of a series of von Frey hairs with logarithmically incremental stiffness (0.6, 1, 1.4, 2, 4, 6, 8, 10, 15, and 26 g; Stoelting, Wood Dale, Ill.) presented perpendicular to the plantar surface for 4-5 seconds each press. The 50% withdrawal threshold of rats in each group was determined by using the up-down method reported by Dixon. As describing above, rats were examined twice in total, once at 1 day before the first injection of PEI, saline, NR1-1 siRNA or MM-NR1-1 siRNA for recoding baseline data, and the other time at 1 day after the injection of CFA for taking the 50% withdrawal threshold after hyperalgesia induction.

Figure 4B:
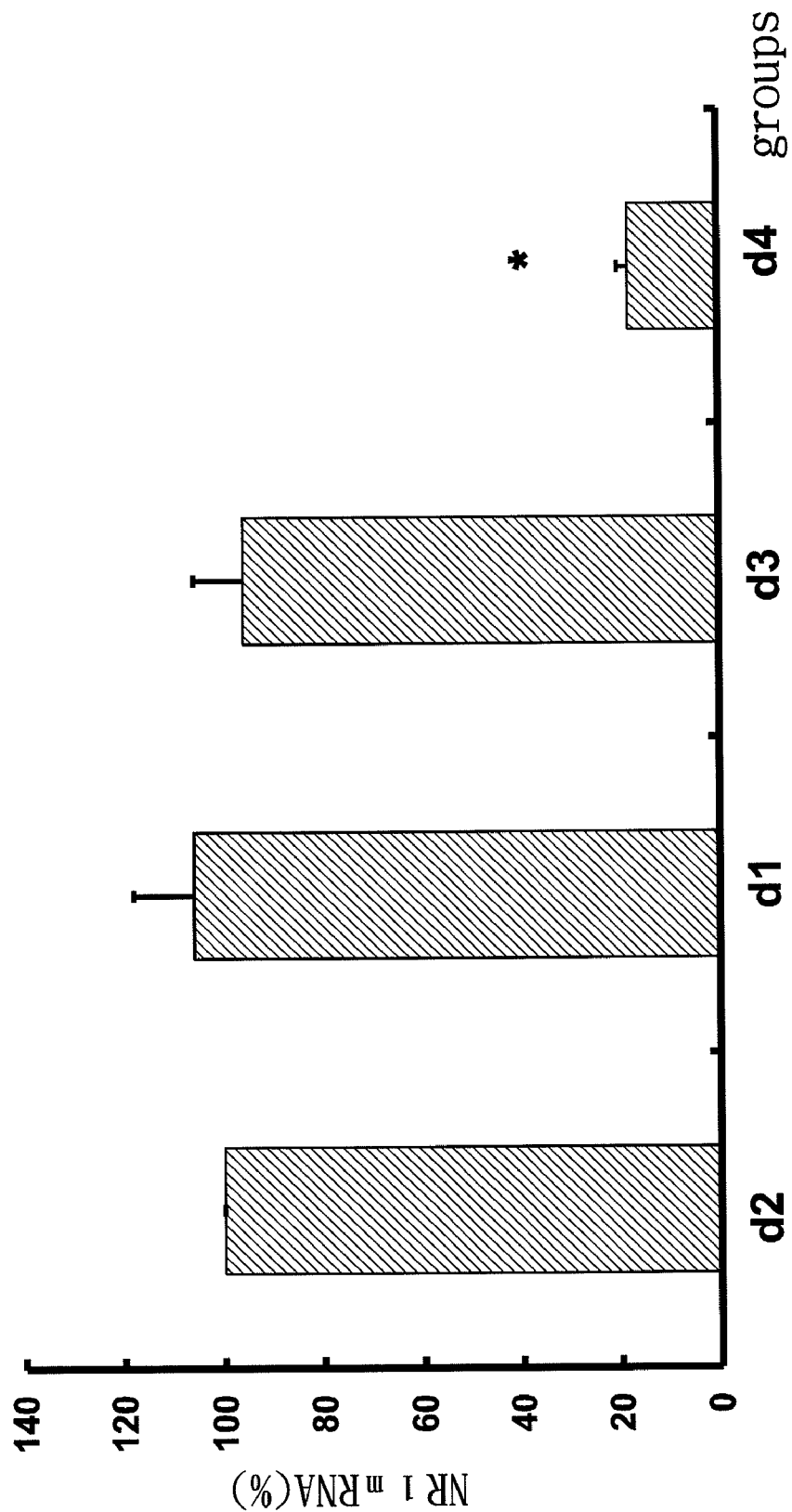
FIG. 4b is a diagram illustrating the mRNA expression level of NR1 in rats' skin tissues after intra-dermal injection of NR1 siRNA and CFA stimulation.

Referring to FIG. 4b illustrates the mRNA expression level of rats' skin tissues in the CFA test. The skin tissues collected from group c4 (treated with 1 nmole NR1-1 siRNA before the CFA test) reveals significant lower level in mRNA expression than that in control groups (d1 and d2) or d3 (with MM-NR1-1 siRNA group treatment). Hence, it is believed the effect of gene knockdown by NR1-1 siRNA to NR1 are specific and well performance in the CFA test, as the injection of NR1-1 mM-siRNA does not make change on NR1 expression.

Figure 4C:
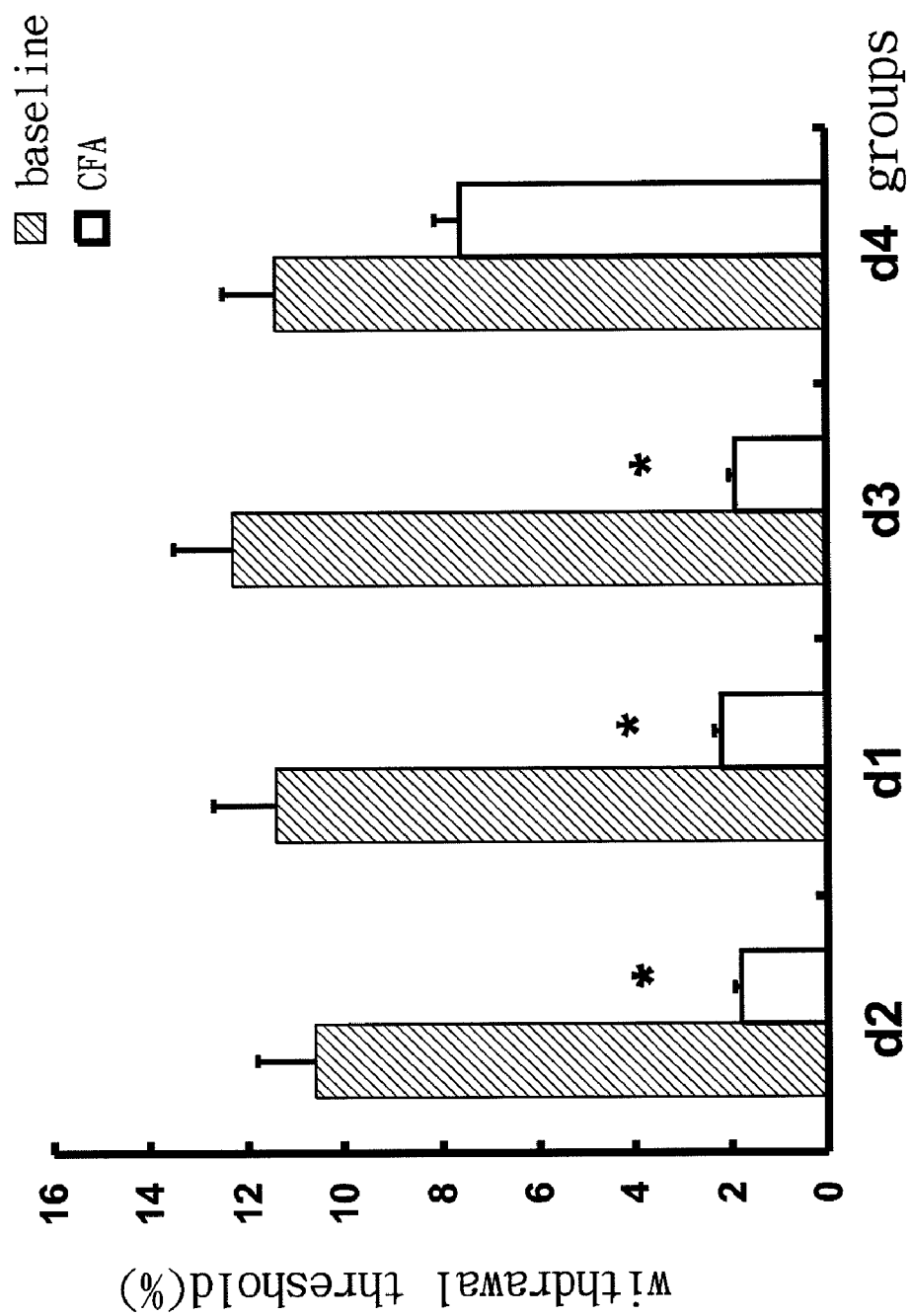
FIG. 4c is a line chart illustrating the frequency of withdrawal thresholds in rats after intra-dermal injection of NR1 siRNA on CFA-induced nociception.

Referring to FIG. 4c summarizes the baseline data and hyperalgesia data of 50% withdrawal threshold of each group rats in the CFA test, wherein the NR1-1 siRNA delivery rats show similar anti-nociception effect on CFA-induced nociception to that on formalin-induced nociception. In the CFA test, the baseline data of 50% withdrawal threshold in rats are around 11 to 12 g among 4 groups but most of them (d1, d2 and d3) go down to 2 g after the mechanical hyperalgesia assay. The decreases of 50% withdrawal threshold in rats indicate that the persistent inflammation pain response caused by CFA induction has resulted in hyperalgesia in rats, therefore, rats becomes more sensitive to other mechanical stimulus. However, in group d4 rats, with delivery of NR1-1 siRNA from subcutaneous injection, shows less decreases of 50% withdrawal threshold in the test (around 3 to 5 g lost only), which also suggests the less degrees of hyperalgesia that rats have undergone. As a result, the anti-nociception effects of NR1-1 siRNA on NR1 are beneficial to moderate the symptom of hyperalgesia induced by CFA injection.

In CFA stimulation test, it is believed that the NMDA receptor NR1 siRNAs in the present invention are well performed in the inhibition of NR1 gene, and according NMDA receptor associated nociception, inflammation pain and hyperalgesia are also diminished. On the other hand, the anti-nociception effects of the NMDA receptor NR1 siRNAs in the present invention are from local effect, in this way it is no longer to bring about any side effects on central nervous system, such as motor coordination.

In summary, the present invention demonstrates that local subcutaneous injection of siRNA targeting the NR1 subunit of the NMDA receptor are effective in silences the expression of the NR1, resulting in significant attenuation of CFA- and formalin-induced nociceptive behaviors. It is suggested that the NMDA receptor NR1 siRNAs in the present invention may provided an anti-nociceptive effect for up to 7 to 14 days without any significant side effects involved, as a result the siRNA may has potential therapeutic value on pharmaceutics for manufacturing the medication of pathological pain relief, especially for clinical patients who suffer from burn, serious skin trauma, inflammation pain and hyperalgesia. The NMDA receptor NR1-related siRNAs in the present invention are able to apply on any creatures via any strategy, by injecting every 7 to 14 days in a dose of 1 to 2 nmole per one for example. Furthermore, the NMDA receptor NR1 siRNAs are allowed to manufacture into any type to medication, such as liquid medicine, tablet or ointment, accompanying with one or more acceptable carrier or adjuvant needed. Consequently, it is highlight the potential of siRNA in the present invention as a valuable tool for the development of new analgesic drugs.

Through the present invention, small interfering RNAs (siRNAs) for gene knockdown of the NDMA receptor NR1 are provided for specifically and regionally inhibiting the gene expression and normal functions of NR1. In this way, it is sufficient to moderate the NR1 related neurotransmission and genetic expression in hypoderm for 7 to 14 days as the subcutaneous injection of the siRNAs in target area. Therefore, it is potential to develop the siRNA mediated medication on pharmaceutics for particular pain or hyperalgesia relieving, which will be highly efficient in improving the quality of clinical medicine and clinical pain treatment, also avoiding the side effects of central nervous system might involved, providing a more powerful and long lasting analgesic drug for people who needed.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A small interfering RNA comprising 21 to 25 ribonucleic acids, wherein the ribonucleic acids are homologous to a RNA sequence of N-methyl-D-aspartate receptor NR1, with the small interfering RNA specifically targeting to subcutaneous N-methyl-D-aspartate receptor NR1 for gene knockdown of N-methyl-D-aspartate receptor NR1 subunit, wherein the sequence of the small interfering RNA are recorded on sequence listing of sequence ID. No. 1 and 2.

2. A small interfering RNA comprising 21 to 25 ribonucleic acids, wherein the ribonucleic acids are homologous to a RNA sequence of N-methyl-D-aspartate receptor NR1, with the small interfering RNA specifically targeting to subcutaneous N-methyl-D-aspartate receptor NR1 for gene knockdown of N-methyl-D-aspartate receptor NR1 subunit, wherein the sequence of the small interfering RNA are recorded on sequence listing of sequence ID. No. 3 and 4.

3. A small interfering RNA comprising 21 to 25 ribonucleic acids, wherein the ribonucleic acids are homologous to a RNA sequence of N-methyl-D-aspartate receptor NR1, with the small interfering RNA specifically targeting to subcutaneous N-methyl-D-aspartate receptor NR1 for gene knockdown of N-methyl-D-aspartate receptor NR1 subunit, wherein the sequence of the small interfering RNA are recorded on sequence listing of sequence ID. No. 5 and 6.

4. A method of managing skin pain, comprising subcutaneously applying the small interfering RNA as defined in claim 1 to skin tissues for temporary interfering with the genetic expression of the NMDA receptor NR1 subunit in hypoderm, and suppressing inflammatory skin pain, wherein the sequence of the small interfering RNA are recorded on sequence listing of sequence ID. No. 1 and 2.

5. The method of managing skin pain as defined in claim 4, wherein the time course of using the small interfering RNA is 7 to 14 days.

6. The method of managing skin pain as defined in claim 4, wherein the dosage of the small interfering RNA is 1 to 2 nmole.

7. A method of managing skin pain comprising subcutaneously applying the small interfering RNA as recorded on sequence listing of sequence ID. No. 3 and 4 to skin tissues for temporary interfering with the genetic expression of the NMDA receptor NR1 subunit in hypoderm, and suppressing inflammatory skin pain, wherein the sequence of the small interfering RNA are recorded on sequence listing of sequence ID. No. 3 and 4.

8. The method of managing skin pain as defined in claim 7, wherein the dosage of the small interfering RNA is 1 to 2 nmole, the time course of using the small interfering RNA is 7 to 14 days.

9. A method of managing skin pain, comprising subcutaneously applying the small interfering RNA as recorded on sequence listing of sequence ID. No. 5 and 6 to skin tissues for temporary interfering with the genetic expression of the NMDA receptor NR1 subunit in hypoderm, and suppressing inflammatory skin pain, wherein the sequence of the small interfering RNA are recorded on sequence listing of sequence ID. No. 5 and 6.

10. The method of managing skin pain as defined in claim 9, wherein the dosage of the small interfering RNA is 1 to 2 nmole, the time course of using the small interfering RNA is 7 to 14 days.

11. An analgesic drug for skin inflammation pain comprising:
a small interfering RNA as defined in claim 1; and
a siRNA acceptable vehicle,
wherein the analgesic drug for skin inflammation pain is used by subcutaneously applying to skin tissues,
wherein the sequences of the small interfering RNA are recorded on sequence listing of sequence ID. No. 1 and 2.

12. The analgesic drug for skin inflammation pain as defined in claim 11, wherein the dosage of the small interfering RNA is 1 to 2 nmole, the time course of using the small interfering RNA is 7 to 14 days.

13. An analgesic drug for skin inflammation pain comprising:
a small interfering RNA as defined in claim 2; and
a siRNA acceptable vehicle,
wherein the analgesic drug for skin inflammation pain is used by subcutaneously applying to skin tissues,
wherein the sequences of the small interfering RNA are recorded on sequence listing of sequence ID. No. 3 and 4.

14. The analgesic drug for skin inflammation pain as defined in claim 13, wherein the dosage of the small interfering RNA is 1 to 2 nmole, the time course of using the small interfering RNA is 7 to 14 days.

15. An analgesic drug for skin inflammation pain comprising:
a small interfering RNA as defined in claim 3; and
a siRNA acceptable vehicle,
wherein the analgesic drug for skin inflammation pain is used by subcutaneously applying to skin tissues,
wherein the sequences of the small interfering RNA are recorded on sequence listing of sequence ID. No. 5 and 6.

16. The analgesic drug for skin inflammation pain as defined in claim 15, wherein the dosage of the small interfering RNA is 1 to 2 nmole, the time course of using the small interfering RNA is 7 to 14 days.

* * * * *

```
                        SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: synthetic small interfering RNA

<400> SEQUENCE: 1
accaggccaa uaagcgacat t                                             21

<210> SEQ ID NO 2
<211> LENGTH: 21
<212> TYPE: DNA
<213> ORGANISM: Artificial Sequence
<220> FEATURE:
<223> OTHER INFORMATION: synthetic small interfering RNA

<400> SEQUENCE: 2
ugucgcuuau uggccuggut t                                             21

<210> SEQ ID NO 3
<211> LENGTH: 21
<212> TYPE: RNA
<213> ORGANISM: Artificial Sequence
<220> FEATURE:
<223> OTHER INFORMATION: synthetic small interfering RNA

<400> SEQUENCE: 3
uguccaucua cucugacaau u                                             21

<210> SEQ ID NO 4
<211> LENGTH: 21
<212> TYPE: RNA
<213> ORGANISM: Artificial Sequence
<220> FEATURE:
<223> OTHER INFORMATION: synthetic small interfering RNA

<400> SEQUENCE: 4
uugucagagu agauggacau u                                             21
```

```
<210> SEQ ID NO 5
<211> LENGTH: 21
<212> TYPE: RNA
<213> ORGANISM: Artificial Sequence
<220> FEATURE:
<223> OTHER INFORMATION: synthetic small interfering RNA

<400> SEQUENCE: 5
uggcaagaau gagucagccu u                                              21

<210> SEQ ID NO 6
<211> LENGTH: 21
<212> TYPE: RNA
<213> ORGANISM: Artificial Sequence
<220> FEATURE:
<223> OTHER INFORMATION: synthetic small interfering RNA

<400> SEQUENCE: 6
ggcugacuca uucuugccau u                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic small interfering RNA

<400> SEQUENCE: 7
accagcgcaa aaacggacat t                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic small interfering RNA

<400> SEQUENCE: 8
uguccguuuu ugcgcuggut t                                              21

<210> SEQ ID NO 9
<211> LENGTH: 17
<212> TYPE: DNA
<213> ORGANISM: Artificial Sequence
<220> FEATURE:
<223> OTHER INFORMATION: synthetic oligonucleotide primer

<400> SEQUENCE: 9
gcgactcccg cagcaat                                                   17

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 10
cccctgccat gttctcaaaa                                                20

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide primer

<400> SEQUENCE: 11
```

-continued

```
tccactcaag gaatcttgtg agatat                                          26

<210> SEQ ID NO 12
<211> LENGTH: 26
<212> TYPE: DNA
<213> ORGANISM: Artificial Sequence
<220> FEATURE:
<223> OTHER INFORMATION: synthetic oligonucleotide primer

<400> SEQUENCE: 12
acttgcccat gtgtatttat ttgttt                                          26

<210> SEQ ID NO 13
<211> LENGTH: 17
<212> TYPE: DNA
<213> ORGANISM: Artificial Sequence
<220> FEATURE:
<223> OTHER INFORMATION: synthetic oligonucleotide primer

<400> SEQUENCE: 13
aaccctcgtg gccgaca                                                    17

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 14
ggtggacaga tgcgggaa                                                   18

<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 15
ggcccagctt ttgaccttag t                                               21

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 16
cctgtgacca ccgcaagag                                                  19

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 17
agggtttctg cattgcccca tt                                              22

<210> SEQ ID NO 18
<211> LENGTH: 20
<212> TYPE: DNA
<213> ORGANISM: Artificial Sequence
```

-continued

```
<220> FEATURE:
<223> OTHER INFORMATION: synthetic oligonucleotide primer

<400> SEQUENCE: 18
tcaccaatca tgccattcca                                          20

<210> SEQ ID NO 19
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 19
cttggctgtt tgccccatt                                           19

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 20
cgtgacagta gctgcggttc c                                        21
```